(12) United States Patent
Nagashima et al.

(10) Patent No.: US 6,841,183 B2
(45) Date of Patent: Jan. 11, 2005

(54) PROCESS FOR PRODUCING ASPARTAME DERIVATIVES, PROCESS FOR PURIFYING ASPARTAME DERIVATIVES, PRODUCTION INTERMEDIATES, AND PROCESS FOR PRODUCING PRODUCTION INTERMEDIATES

(75) Inventors: Kazutaka Nagashima, Kawasaki (JP); Shinji Fujita, Kawasaki (JP); Yuuichi Aoki, Kawasaki (JP); Shigeru Kawahara, Kawasaki (JP); Tadashi Takemoto, Kawasaki (JP); Eriko Ono, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 13 days.

(21) Appl. No.: 10/108,426

(22) Filed: Mar. 29, 2002

(65) Prior Publication Data

US 2002/0127320 A1 Sep. 12, 2002

Related U.S. Application Data

(63) Continuation of application No. PCT/JP00/06625, filed on Sep. 26, 2000.

(30) Foreign Application Priority Data

| Oct. 7, 1999 | (JP) | 11-287399 |
| Oct. 7, 1999 | (JP) | 11-287400 |
| Oct. 8, 1999 | (JP) | 11-288206 |

(51) Int. Cl.[7] .............................................. A23L 1/236
(52) U.S. Cl. .......................... 426/548; 560/37; 560/40; 560/41
(58) Field of Search ............................ 426/548; 560/37, 560/40, 41

(56) References Cited

FOREIGN PATENT DOCUMENTS

| EP | 1 245 573 | 10/2002 |
| JP | 63-203677 | 8/1988 |
| WO | WO 87/00840 | 2/1987 |
| WO | 94/11391 | 5/1994 |
| WO | WO 99/52937 | 10/1999 |
| WO | WO 00/00508 | 1/2000 |
| WO | WO 00/17230 | 3/2000 |

OTHER PUBLICATIONS

J.A. Panetta, et al., "New Syntheses of Coumarins", J. Org. Chem., vol. 47, No. 6, 1982, pp. 946–950.

N. Cohen, et al., "Lewis Acid Mediated Nucleophillic Substitution Reactions of 2–Alkoxy–3,4–dihydro–2H–1– benzopyrans: Regiochemistry and Utility in the Synthesis of 3,4–Dihydro–2H–1–benzopyran–2–carboxylic Acids", J. Org. Chem., vol. 54, No. 14, 1989, pp. 3282–3292.

*Primary Examiner*—Leslie Wong
(74) *Attorney, Agent, or Firm*—Oblon, Spivak, McClelland, Maier & Neustadt, P.C.

(57) ABSTRACT

N-[N-[3-(2-hydroxy-substituted phenyl)propyl]-L-α-aspartyl]-L-phenylalanine 1-methyl ester derivatives, which are useful as sweeteners, may be conveniently produced by subjecting a 2-hydroxychroman derivative having various substituents on the benzene ring and aspartame to a reductive alkylation reaction. These compounds may be purified by subjecting such a derivative containing one or more impurities to a crystallization step to crystallize the same. Further, there are provided a process for producing dialkoxychroman derivatives useful as intermediates for the production of such aspartame derivatives in the above process, and novel dialkoxychroman derivatives thus produced, which are excellent as the production intermediate.

9 Claims, 3 Drawing Sheets

PROCESS FOR PRODUCING ASPARTAME DERIVATIVES, PROCESS FOR PURIFYING ASPARTAME DERIVATIVES, PRODUCTION INTERMEDIATES, AND PROCESS FOR PRODUCING PRODUCTION INTERMEDIATES

CROSS REFERENCES TO RELATED APPLICATIONS

This application is a continuation of PCT International Application No. PCT/JP00/06625, which was filed on Sep. 26, 2000, and which is incorporated herein by reference in its entirety. This application also claims priority to Japanese Patent Application Nos. 11-287399, 11-287400, and 11-288206, which were filed on Oct. 7, 1999, Oct. 7, 1999, and Oct. 8, 1999, respectively, and which are incorporated herein by reference in their entireties.

BACKGROUND OF THE INVENTION

1. Field of the Invention

The present invention relates to novel processes for producing N-[N-[3-(2-hydroxy-substituted phenyl)propyl]-L-α-aspartyl]-L-phenylalanine 1-methyl ester derivatives which are important as sweeteners.

The present invention further relates to novel processes for producing high-purity products of N-[N-[3-(2-hydroxy-4-substituted phenyl)propyl]-L-α-aspartyl]-L-phenylalanine 1-methyl ester derivatives which are especially important among the sweeteners described above. More specifically, the present invention relates to: (1) processes for purifying such derivatives which may contain various impurities; (2) processes for producing high-purity products of such derivatives using an especially excellent simple crystallization method; and (3) crystals of the derivatives which can be thus obtained.

Still further, the present invention relates to novel processes for producing various intermediates which are useful for the production of the foregoing derivatives, especially dialkoxychroman derivatives which have been found to be useful as production intermediates of aspartyl dipeptide ester derivatives (aspartame derivatives) that are especially excellent as sweeteners and have a high degree of sweetness. More specifically, it relates to processes for producing specific dialkoxychroman derivatives from resorcinol and an acrolein dialkyl acetal in two stages at good efficiency, and novel dialkoxychroman derivatives which can be obtained by such a process and are especially preferable intermediates.

2. Discussion of the Background

In recent years, the importance of good eating habits to health has been increasingly recognized, and especially fatness or obesity caused by an excessive intake of sugar and the diseases accompanied by the fatness have become an issue. Therefore, the development of a low-calorie sweetener that replaces sugar has been in demand. As a sweetener that is widely used at present, there is aspartame which is excellent in terms of safety and quality of sweetness. Nevertheless, it has been somewhat problematic in a stability. Under these circumstances, some of the present inventors have newly found N-[N-[3-(2-hydroxy-substituted phenyl)propyl]-L-α-aspartyl]-L-phenylalanine 1-methyl ester derivatives to be sweeteners which are excellent in stability and very high in sweetness, namely superior in cost for sweetness in comparison with aspartame. N-[N-[3-(2-hydroxy-4-substituted phenyl)propyl]-L-α-aspartyl]-L-phenylalanine 1-methyl ester derivatives are especially preferable, and N-[N-[3-(2-hydroxy-4-methoxyphenyl)propyl]-L-α-aspartyl]-L-phenylalanine 1-methyl ester is an even more preferable compound.

As a process for producing a foregoing novel N-[N-[3-(2-hydroxy-substituted phenyl)propyl]-L-α-aspartyl]-L-phenylalanine 1-methyl ester derivative, a process which comprises reductively alkylating β-O-benzyl-α-L-aspartyl-L-phenylalanine methyl ester with 2-benzyloxy-substituted cinnamaldehyde derivative and $NaB(OAc)_3H$, and then removing the benzyl group as a protecting group, and reducing of a double bond therein has been discovered by some of the present inventors. However, according to this process, the formation of the starting material is intricate, and further the reactions such as the reductive alkylation, the deprotection and the like have to be conducted separately. Thus, it requires steps that are somewhat intricate industrially.

Meanwhile, apart from the investigations of the present inventors, similar compounds in which an alkyl group is introduced into an amino group of the aspartic acid constituting aspartame have been studied, and are described in the Kokai publication of the International Patent Application No. WO94/11391. This publication describes N-[N-[3-(3-methoxy-4-hydroxyphenyl)propyl]-L-α-aspartyl]-L-phenylalanine 1-methyl ester which is relatively similar in structure to the N-[N-[3-(2-hydroxy-substituted phenyl)propyl]-L-α-aspartyl]-L-phenylalanine 1-methyl ester derivatives that the present inventors have found. However, a specific description of not only the starting material but also by what method the production was conducted is not provided at all in this publication.

Under these circumstances, the development of an industrially advantageous process for producing the foregoing derivative(s) has been in demand.

Thus, one problem to be solved by the present invention is to provide a practically and industrially advantageous process for producing N-[N-[3-(2-hydroxy-substituted phenyl)propyl]-L-α-aspartyl]-L-phenylalanine 1-methyl ester derivatives that are excellent sweeteners having a high degree of sweetness.

Next, as stated above, an excellent process for purifying the derivatives which have newly been found by some of the present inventors as sweeteners having a high degree of sweetness is unknown.

As a process for purifying the novel N-[N-[3-(2-hydroxy-4-substituted phenyl)propyl]-L-α-aspartyl]-L-phenylalanine 1-methyl ester derivative, for example, a process in which a reaction concentrated solution containing the desired compound of the present invention is purified by preparative thin layer chromatography (PTLC) has been employed. In this case, in the final form of the desired compound, extracted fractions of the desired compound are simply concentrated to dryness. Nevertheless, since this purification process involves silica gel column chromatography, when it is performed industrially, it incurs high costs and involves environmental problems such as waste silica gel and the like. Furthermore, when the final form of the desired compound is not a crystal but a mere solid, there is also the problem in view of a consumers' safety, such as decomposition after the delivery of the products or the like. Thus, a practical and industrial purification process of the desired compound is not at all established. Accordingly, the development of a process for producing the foregoing sweetener(s) having a high degree of sweetness in a state of a high purity, preferably in a crystallized state has been in demand.

Sweeteners are mainly used in foods or pharmaceuticals, and consumed by people. Thus, they have to be purified by a method which yields high-purity products actually free from impurity(ies) or decomposed substance(s). Moreover, in the case of peptide sweeteners which are relatively easily decomposable, such as the desired compounds of the present invention, a final form having a better stability is desired for preventing decomposition after the delivery of the products.

Therefore, the present inventors have conducted studies on the acquisition or the formation of high-purity products, especially crystals that are a better form in regard to stability as products, by purifying the desired compounds of the present invention through crystallization using a crystallization method.

Thus, another problem to be solved by the present invention is also to provide a practical and industrial process for purifying N-[N-[3-(2-hydroxy-4-substituted phenyl)propyl]-L-α-aspartyl]-L-phenylalanine 1-methyl ester derivatives which are excellent as sweeteners and have a high degree of sweetness, especially a process for obtaining the high-purity desired compounds as crystals from impurity(ies) contained therein, and crystals which are a final form having better stability as products.

Moreover, further investigations of the present inventors have revealed that the development of an industrially superior process for producing the aspartyl dipeptide ester derivatives (aspartame derivatives) which are excellent as sweeteners and have a high degree of sweetness, especially the development of excellent intermediates which are useful for the production thereof is required.

Accordingly, another problem to be solved by the present invention is also to develop a process for producing the aspartyl dipeptide ester derivatives (aspartame derivatives) industrially and advantageously, and especially to provide compounds which are excellent as intermediates useful for the as production thereof and a simple process for producing the same.

SUMMARY OF THE INVENTION

Accordingly, it is one object of the present invention to provide novel processes for producing N-[N-[3-(2-hydroxy-substituted phenyl)propyl]-L-α-aspartyl]-L-phenylalanine 1-methyl ester derivatives which are important as sweeteners.

It is another object of the present invention to provide novel processes for producing such N-[N-[3-(2-hydroxy-4-substituted phenyl)propyl]-L-α-aspartyl]-L-phenylalanine 1-methyl ester derivatives as high-purity products.

It is another object of the present invention to provide novel processes for purifying such derivatives which may contain various impurities.

It is another object of the present invention to provide novel processes for producing such derivatives in high-purity by using an especially excellent simple crystallization method.

It is another object of the present invention to provide novel crystals of such derivatives.

It is another object of the present invention to provide novel processes for producing various intermediates which are useful for the production of the foregoing derivatives.

It is another object of the present invention to provide novel processes for producing dialkoxychroman derivatives which have been found to be useful as intermediates for the production of aspartyl dipeptide ester derivatives (aspartame derivatives) that are especially excellent as sweeteners and have a high degree of sweetness.

It is another object of the present invention to provide novel processes for producing specific dialkoxychroman derivatives from resorcinol and an acrolein dialkyl acetal in two stages at good efficiency.

It is another object of the present invention to provide novel dialkoxychroman derivatives which can be obtained by such a process and are especially preferable intermediates.

These and other objects, which will become apparent during the following detailed description, have been achieved by the present inventors' discovery that an N-[N-[3-(2-hydroxy-substituted phenyl)propyl]-L-α-aspartyl]-L-phenylalanine 1-methyl ester derivative can be produced in high yield at good efficiency by a process comprising:

subjecting a 2-hydroxychroman derivative (3,4-dihydro-substituted-2H-1-benzopyran-2-ol derivative) having various substituents in a benzene ring therein and aspartame to a reductive alkylation reaction.

This finding has led to the completion of an aspect of the present invention ("a process for producing an aspartame derivative") which is included as one embodiment of the present invention.

Further, the present inventors have studied a process for purifying the aspartame derivative, more specifically a purification process including a process for producing the desired compound in a high purity from a N-[N-[3-(2-hydroxy-4-substituted phenyl)propyl]-L-α-aspartyl]-L-phenylalanine 1-methyl ester derivative containing impurity(ies) present or a crystallization process. They have found that with respect to the derivatives represented by general formula (3) to be described later among the foregoing desired compound derivatives, high-purity products of the desired compounds can be produced simply by a crystallization process in particular, and the derivatives can therefore be purified at good efficiency and besides they can be isolated in the form of high-purity crystals. These findings have led to the completion of another aspect of the present invention ("a process for purifying an aspartame derivative") which is another embodiment of the present invention.

Still further, the present inventors have studied intermediates useful for the production of the aspartame derivatives, especially N-[N-[3-(2-hydroxy-4-methoxyphenyl)propyl]-L-α-aspartyl]-L-phenylalanine 1-methyl ester, and have consequently found that a 2-alkoxy-7-methoxychroman is extremely excellent as an production intermediate.

Moreover, the present inventors have found a process in which a 2-alkoxy-7-methoxychroman can be produced in a high yield at a low cost by using, as a starting material, resorcinol, which is less costly and easily obtainable in comparison with 3-methoxyphenol, reacting the resorcinol with an acrolein dialkyl acetal in the presence of an acid catalyst and then methylating a phenolic hydroxyl group therein as shown below, and that this process has therefore an industrial superiority. On the basis of these findings, the present inventors have come to complete another aspect of the present invention ("a process for producing a production intermediate") which is still another embodiment of the present invention. Incidentally, as one example, it is shown below that the 2-position in the dialkoxychroman derivative is an ethoxy form based on an ethyl group. However, alkoxy forms based on other lower alkyl groups are also available.

Furthermore, it has also been found that the 2-alkoxy-7-methoxychromans (alkoxy group: lower alkyloxy group) may be used as various intermediates useful for the production of products such as the above-described aspartame derivatives and also pharmaceuticals, food and others. These various findings have led to the completion of another aspect of the present invention ("a process for using a production intermediate") which is still another embodiment of the present invention.

BRIEF DESCRIPTION OF THE DRAWINGS

A more complete appreciation of the present invention and many of the attendant advantages will be readily obtained as the same becomes better understood by reference to the following detailed description when considered in connection with the accompanying drawings wherein.

DETAILED DESCRIPTION OF THE PREFERRED EMBODIMENTS

Thus, in a first aspect, the present invention provides a process for producing an aspartame derivative, comprising:

subjecting a 2-hydroxychroman derivative having various substituents in a benzene ring as represented by the following general formula (1) and aspartame to a reductive alkylation reaction in the presence of a catalyst using a solvent, to produce an N-[N-[3-(2-hydroxy-substituted phenyl)propyl]-L-α-aspartyl]-L-phenylalanine 1-methyl ester derivative represented by the following general formula (2).

(1)

(2)

In the formulas (1) and (2), $R_1$, $R_2$, $R_3$, and $R_4$, independently from each other, each represent a substituent selected from a hydrogen atom, a hydroxyl group, an alkoxy group having 1 to 3 carbon atoms, a benzyloxy group, an alkyl group having 1 to 3 carbon atoms and a hydroxyalkyloxy group having 2 or 3 carbon atoms, and further $R_1$ and $R_2$ and/or the two $R_3$ and $R_4$, or the two $R_2$ and $R_3$ in combination may represent a methylenedioxy group. For example, when $R_1$ and $R_2$ are combined to form a methylenedioxy group, the two $R_3$ and $R_4$ in combination may represent a methylenedioxy group or may not be combined. When these are not combined, $R_1$ and $R_2$ have the same meaning as the foregoing $R_1$ and $R_2$. This is also the same with the meaning of $R_1$ and $R_2$ when $R_3$ and $R_4$ are combined. Meanwhile, when $R_2$ and $R_3$ in combination represent a methylenedioxy group, $R_1$ and $R_4$ have the same meaning as the foregoing $R_1$ and $R_4$ respectively.

Further, in formula (2), none of $R_1$, $R_2$, $R_3$ and $R_4$ represents a benzyloxy group. The reason is that when any of $R_1$, $R_2$, $R_3$ and $R_4$ represents a benzyloxy group in general formula (1), it is converted into a hydroxyl group by debenzylation of the benzyl group of the benzyloxy moiety in the production of desired compound by the reaction in the present invention.

Typical and more preferable processes in the case of producing aspartame derivatives in the present invention are described below. These are naturally included in the present invention. However, the present invention is not limited to these unless the gist of the present invention is deviated from.

2-Hydroxychroman derivatives having various substituents on the benzene ring are important starting materials used in the present processes and can be formed using known techniques or can be procured. For example, these derivative can be formed easily at a low cost according to a known process (see *J. Org. Chem.*, vol. 47, p. 946 (1982) and *J. Org. Chem.*, vol. 54, p. 3282 (1989), which are incorporated herein by reference, and the like), by subjecting a corresponding substituted phenol and an acrolein acetal derivative or an allene derivative to a cyclization reaction in the presence of an acid catalyst to form a cyclic acetal, and then conducting an acid hydrolysis thereof. In a preferred embodiment, 2-hydroxy-7-methoxychroman can be formed more easily and at a low cost by adopting a process for producing this production intermediate according to the present invention.

The resulting 2-hydroxychroman derivative having various substituents on the benzene ring and aspartame are subjected to a reductive alkylation reaction with hydrogen in a solvent that dissolves these compounds, for example, an organic solvent (a single solvent made of one type or a mixed solvent made of plural types) or a mixed solvent of such an organic solvent and water, in the presence of a reductive alkylation catalyst, for example, a hydrogenation catalyst, preferably conducting the reductive alkylation reaction under an appropriate or effective reaction temperature and pressure. Thus, an N-[N-[3-(2-hydroxy-substituted phenyl)propyl]-L-α-aspartyl]-L-phenylalanine 1-methyl ester derivative as a desired compound can be produced in a high yield with good efficiency.

Further, after the completion of the reaction, the catalyst is removed by filtration or the like, and a high-purity N-[N-[3-(2-hydroxy-substituted phenyl)propyl]-L-α-aspartyl]-L-phenylalanine 1-methyl ester derivative can also be obtained by a purification method such as chromatographic purification, crystallization or the like as required. In an especially preferred embodiment, the N-[N-[3-(2-hydroxy-4-substituted phenyl)propyl]-L-α-aspartyl]-L-phenylalanine 1-methyl ester is purified by a process for purifying an aspartame derivative according to the present invention.

Any organic solvent that dissolves starting materials or the product may be used in the reductive alkylation reaction. For example, at least one selected from among methanol, ethanol, isopropyl alcohol, tetrahydrofuran, acetonitrile, acetic acid, and ethyl acetate, or a mixed solvent of at least one of these organic solvents and water can be used as a preferable solvent. Alcohols are more preferable, methanol is further preferable in view of the cost, and a mixed solvent of methanol and water is further more preferable. When a mixed solvent of the organic solvent and water is used, the composition ratio of the two components involved therein is not particularly limited. It is advisable that aspartame, the 2-hydroxychroman derivative having various substituents in the benzene ring and the N-[N-[3-(2-hydroxy-substituted phenyl)propyl]-L-α-aspartyl]-L-phenylalanine 1-methyl ester derivative product are fully dissolved in the solvent.

As the catalyst used in the reductive alkylation reaction, a general hydrogenation catalyst, for example, a palladium based catalyst such as palladium carbon or the like, a platinum based catalyst such as platinum carbon or the like, a rhodium based catalyst such as rhodium-alumina or the like, or a nickel based catalyst such as Raney nickel or the like can be used. The amount of the catalyst used is not particularly limited. For example, in case of 10% palladium carbon (water content 50%), it is advisable to use the same in the range of 1/100 to 1/3 or so in terms of a weight ratio based on the aspartame.

The reaction can be conducted by hydrogenation. At this time, the reaction satisfactorily proceeds at a hydrogen pressure of 0.1 MPa. The reaction can also be conducted at a hydrogen pressure of 0.1 to 1.0 MPa or so.

With respect to the reaction temperature, the reaction easily proceeds at room temperature, preferably at 10 to 30° C. However, in order to improve the solubility of starting materials or the product or to improve the reaction rate by suppressing a side reaction, the reaction can also be conducted by raising the temperature to 60° C. or so. Preferably, the reaction is carried out at a temperature range of 20 to 50° C. or so, more preferably the range of 25 to 45° C. or so.

Although the reaction time is not particularly limited, it is advisable to conduct the reaction for a time in the range of 2 to 72 hours or so.

With respect to the molar ratio of the 2-hydroxychroman derivative having various substituents in the benzene ring and the aspartame used as the starting materials of the reaction, the reaction can be conducted preferably in the range of 0.5 to 2 or so moles of the 2-hydroxychroman derivative per one mole of aspartame.

As the compounds obtained by this process, the compounds obtained by the following process can be mentioned in particular.

1. The compound of formula (2) in which in the general formulas (1) and (2), $R_2$ is a methoxy group, and $R_1$, $R_3$ and $R_4$ are hydrogen atoms.
2. The compound of formula (2) in which in the general formulas (1) and (2), $R_2$ is a hydroxyl group, and $R_1$, $R_3$ and $R_4$ are hydrogen atoms, provided that $R_2$ in formula (1) may be a benzyloxy group.
3. The compound of formula (2) in which in the general formulas (1) and (2), $R_2$ is a methyl group, and $R_1$, $R_3$ and $R_4$ are hydrogen atoms.
4. The compound of formula (2) in which in the general formulas (1) and (2), $R_1$, $R_2$, $R_3$ and $R_4$ are, independently from each other, a substituent selected from the group consisting of a hydrogen atom, a hydroxyl group, a methoxy group, a benzyloxy group, a methyl group, and a hydroxyalkyloxy group having 2 or 3 carbon atoms, and the two $R_1$ and $R_2$ and/or the two $R_3$ and $R_4$, or the two $R_2$ and $R_3$ in combination may represent a methylenedioxy group, provided that in formula (2), none of $R_1$, $R_2$, $R_3$ and $R_4$ represents a benzyloxy group.

In another aspect, the present invention provides a process for purifying an aspartame derivative. The process of purifying an aspartame derivative according to the present invention lies in a process for producing an N-[N-[3-(2-hydroxy-4-substituted phenyl)propyl]-L-α-aspartyl]-L-phenylalanine 1-methyl ester derivative, characterized by subjecting the N-[N-[3-(2-hydroxy-4-substituted phenyl)propyl]-L-α-aspartyl]-L-phenylalanine 1-methyl ester derivative represented by the following general formula (3) and containing impurity(ies) to a crystallization step to crystallize the derivative.

(3)

wherein $R_2$ represents a substituent selected from the group consisting of a methoxy group, a hydroxyl group, and a methyl group.

By this process, a high-purity product can be obtained.

The N-[N-[3-(2-hydroxy-4-substituted phenyl)propyl]-L-α-aspartyl]-L-phenylalanine 1-methyl ester derivative containing impurity(ies) may be in the form of a solution, a solid, or an intermediate therebetween such as a slurry, which contains the derivative.

For crystallizing a derivative from the derivative containing impurity(ies) by the purification process of the present invention, it is advisable to conduct the crystallization by crystallizing the desired compound (an aspartame derivative as a compound to be purified) through a crystallization step in an appropriate crystallization solvent. This procedure can purify the desired compound and isolate the high-purity desired compound as crystals.

The desired compound contains, in many cases, at least one of aspartame, aspartame derivative(s), peptide derivative(s), amino acid(s), amino acid derivative(s) and 2-hydroxy-7-substituted chroman derivative (3,4-dihydro-7-substituted-2H-1-benzopyran-2-ol derivative) represented by the following general formula (4) as impurity(ies). The purification process of the present invention is suitable for purifying the desired compound (compound to be purified) containing such impurity(ies). The compound to be purified may be in a the solution state, the solid state and, as required, the intermediate state thereof as noted above, and its state is not particularly limited so long as the impurities(y) are contained therein.

Incidentally, in the formula (4), $R_2$ represents a substituent selected from the group consisting of a methoxy group, a hydroxyl group, and a methyl group. In formula (4), $R_2$ may further represent a benzyloxy group.

The characteristic feature of the process for purifying the aspartame derivative in the present invention is that with respect to the compound to be purified which contains impurity(ies), regardless of the state of the desired compound, the desired compound is crystallized using an appropriate crystallization solvent to produce a high-purity product and, as required, the crystals are separated for purification.

As a typical example of the compound to be purified, a reaction solution containing the desired compound obtained by conducting the reductive alkylation reaction for producing the desired compound using aspartame and the 2-hydroxy-7-substituted chroman derivative represented by the general formula (4) can be mentioned. With respect to the compound to be purified in such a solution state, when purifying the same from a reaction solution containing an insoluble matter undesirable in conducting the crystallization step, for example, a catalyst used or the like, the solid may be is removed in advance by separation through filtration or the like. The thus-obtained solution is subjected to a crystallization step under a condition appropriate for crystallization of the desired compound (compound to be purified), whereby the desired compound can be crystallized and consequently separated for purification.

Incidentally, in the formula (4), $R_2$ represents, as noted above, a substituent selected from a methoxy group, a hydroxyl group and a methyl group. In the formula (4), $R_2$ may further represent a benzyloxy group. This is because when the desired compound, namely the compound represented by the formula (3) is produced by using the compound of formula (4) in which $R_2$ is a benzyloxy group as the starting material along with aspartame, the benzyloxy moiety of the $R_2$ is converted into a hydroxyl group by debenzylation of a benzyl group in the reaction.

For example, when the solution contains a solvent appropriate as a crystallization solvent for the desired compound (aspartame derivative), the desired compound can be crystallized by a method in which the solution is concentrated to a condition appropriate for crystallization of the desired compound by vacuum concentration or the like, or in which after the concentration an appropriate crystallization solvent is specifically selected from among crystallization solvents available for crystallization of the desired compound and secondarily added to the concentrated material in an amount up to a condition appropriate for crystallization and cooling is conducted therefor as required, or in which after the concentration the concentrated material is cooled to a temperature appropriate for crystallization, or the like.

Meanwhile, for example, when the solution is a solvent inappropriate as a crystallization solvent of the desired compound, it is possible that the solvent is completely removed by distillation, by vacuum concentration or the like, for solidification, an appropriate crystallization solvent specifically selected from among crystallization solvents of the desired compound is added and the desired compound is crystallized by the same crystallization method as in the foregoing case. Naturally, this method can also be applied to the case where the compound to be purified does not contain a solvent. Further, whether or not the solution contains a crystallization solvent for the desired compound, such a solvent substitution method is also an effective method.

When the foregoing compound to be purified contains peptide derivative(s) such as aspartame and the like as impurity(ies) mixed therein, a step of separating such impurity(ies) before the crystallization, for example, separation by filtration of aspartame or the like precipitated in replacing a solvent in the above-formed (synthetic) reaction solution with an appropriate organic solvent is also effective for the subsequent crystallization of the desired compound.

As the solvent used in the crystallization step in this method, at least one selected from among lower alcohols such as methanol, ethanol, isopropyl alcohol, and the like, ketones such as acetone, methyl ethyl ketone, methyl isobutyl ketone, and the like, esters such as methyl acetate, ethyl acetate, propyl acetate (n-propyl acetate, isopropyl acetate, and the like), butyl acetate, and the like, tetrahydrofuran and acetonitrile, or a mixed solvent of at least one of these organic solvents and water can be used as a preferable solvent.

The crystallization method used for the crystallization step in this purification process is not particularly limited. However, for readily solving the problem before the purification process of the present invention, it can preferably be performed by a method including a combination of, for example, partial or complete solvent removal by concentration, addition of the crystallization solvent described above and crystallization with cooling. As a more specific example, when the substance to be purified is that in the synthetic reaction solution containing the N-N[-[3-(2-hydroxy-4-methoxyphenyl)propyl]-L-α-aspartyl]-L-phenylalanine 1-methyl ester obtained by reductively alkylating aspartame and 2-hydroxy-7-methoxychroman (3,4-dihydro-7-methoxy-2H-1-benzopyran-2-ol) in a mixed solvent of methanol and water (mixing ratio 3:2 v/v), the crystals of the high-purity desired compound can be obtained by quite a simple method in which the catalyst used is separated by filtration therefrom, methanol is then partially removed by vacuum concentration at 40° C. therefrom, the desired compound is crystallized by cooling the concentrated material to 5° C., and the crystals precipitated are separated. The method for separating the crystals is not particularly limited, and a general method such as separation by filtration, centrifugal separation, and the like can be used. Further, after the separation of the crystals, the crystals can be dried as required. This drying method is not particularly limited either, and a general method such as vacuum drying, air drying and the like can be used.

A single set of conditions appropriate for crystallization of the desired compound in this purification process cannot generally be described because the conditions may vary depending on a combination of the identity of the desired compound, the type of the crystallization solvent, the amount of the solvent used, the crystallization method and the like. However, based on the teachings in the present specification, one of skill in the art can easily choose appropriate conditions. For details, refer to the Examples (item of purification process or method) below.

Thus in another aspect, the present invention provides the crystals per se of a desired compound (an aspartame derivative) obtained by the purification process of the present invention described above. In preferred embodiments, the present invention provides crystals of the desired compound showing the following physical properties.

1) Crystals of N-[N-[3-(2-hydroxy-4-methoxyphenyl) propyl]-L-α-aspartyl]-L-phenylalanine 1-methyl ester which, when measured by powder X-ray diffractometry, show X-ray diffraction peaks in at least diffraction angles (2θ, CuKα rays) of 6.1°, 15.8°, 19.7°, and 21.6°.

2) Crystals of N-[N-[3-(2,4-dihydroxyphenyl)propyl]-L-α-aspartyl]-L-phenylalanine 1-methyl ester which, when measured by powder X-ray diffractometry, show X-ray diffraction peaks in at least diffraction angles (2θ, CuKα rays) of 5.5°, 19.0°, 19.7°, and 21.2°.

3) Crystals of N-[N-[3-(2-hydroxy-4-methylphenyl) propyl]-L-α-aspartyl]-L-phenylalanine 1-methyl ester which, when measured by powder X-ray diffractometry, show X-ray diffraction peaks in at least diffraction angles (2θ, CuKα rays) of 5.0°, 14.5°, 19.0°, and 19.6°.

The 2-hydroxychroman derivatives having various substituents in a benzene ring can be formed using a known technique or procured. Thus, the 2-hydroxy-7-substituted chroman derivatives can be formed (synthesized) easily at low costs according to a known method (see *J. Org. Chem.*, vol. 47. p. 946 (1982), and *J. Org. Chem.*, vol. 54, p. 3282 (1989), which are incorporated herein by reference, or the like), by subjecting a corresponding substituted phenol and an acrolein acetal derivative or an allene derivative to a cyclization reaction in the presence of an acid catalyst to form a cyclic acetal and then conducting an acid hydrolysis of the acetal.

However, in a preferred embodiment, 2-hydroxy-7-methoxychroman can be formed (synthesized) more easily at a low cost by adopting the process for producing production intermediate in the present invention thereto.

Subsequently, according to the process for producing the aspartame derivative in the present invention, the resulting 2-hydroxy-7-substituted chroman derivative and aspartame are subjected to a reductive alkylation reaction with hydrogen in a solvent that dissolves these, for example, a solvent such as alcohol, hydrous alcohol or the like in the presence of a reductive alkylation catalyst, for example, a palladium based, a platinum based or a rhodium based hydrogenation catalyst, and preferably to reductive alkylation reaction at an appropriate or effective reaction temperature and pressure, whereby an N-[N-[3-(2-hydroxy-4-substituted phenyl) propyl]-L-α-aspartyl]-L-phenylalanine 1-methyl ester derivative as a desired compound can be produced in a high yield at a good efficiency.

The purification process of the present invention is performed using the thus-obtained derivative as compound to be purified, whereby the various impurities present in the reaction system can be separated to be able to produce a high-purity product. Consequently, the purification process of the present invention is extremely appropriate for conducting the purification after the reaction for formation (synthesis) thereof.

The thus-obtained crystals can be used as sweeteners for animals, especially for humans, in foods and drinks having a sweetness and other products requiring a sweetness (sweet taste). A sweetener, and a food and drink or another product having a sweetness can be provided by containing or adding at least one type (plural types are also possible) of the crystals of the thus-obtained compounds as an active ingredient.

In this case, a carrier and/or a filler (bulking agent) for sweeteners may further be incorporated therein.

Moreover, it is also possible to provide a method for imparting a sweetness by adding or containing at least one type of the crystals to or in a product such as a food and drink, and the like required to have a sweetness, or an intermediate product thereof during the production thereof.

These usages and methods are also included as aspects of the present invention.

In the case of producing sweeteners, producing products such as food and drink and the like having a sweetness (including pharmaceuticals and others) or imparting a sweetness to products or intermediate products thereof requiring a sweetness, it can be conducted by means of any known or conventional method for producing sweeteners with a sweet ingredient or for imparting a sweetness, and the like.

When the crystals obtained in the present invention are used as sweeteners or in a food or drink, a carrier, a thickener, a filler and/or an excipient for the sweetener can also be used, as required, for more stabilization as noted above. In this case, for example, any known or conventional carrier, thickener, filler, excipient and the like for sweeteners can be used.

As the carrier and the like, saccharides and the like usable as stabilizers can also be used, and other products which have been so far used or can be used as a carrier for sweeteners can also be used.

The product can be formed in the form of a sweetener. Further, it can be formed in the form of a food or drink such as ices (frozen dessert and the like) and the like, other than the form of a sweetener, by using any ingredient(s) or excipient(s) necessary for a food or drink.

Moreover, the crystals can also be used as sweeteners in various products such as foods and drinks and the like required to have a sweetness, for example, confectionery (ices, jellies, cakes and candies), bread, a chewing gum, sanitary products (hygiene products), toiletries (cosmetics, including oral compositions such as a toothpaste), pharmaceuticals (drugs), products for animals except humans, and so forth. Thus, the crystals obtained in the present invention can be used in the form of products having a sweetness and in a method for imparting a sweetness to these products required to have a sweetness.

In another aspect, the present invention provides a process for producing certain production intermediates. The process for producing the production intermediate according to the present invention is a process for producing a 2-alkoxy-7-methoxychroman (III), characterized by reacting a resorcinol (I) with an acrolein dialkyl acetal (II) in the presence of an acid catalyst to form a 2-alkoxy-7-hydroxychroman, and then subjecting this compound to a reaction of methylating (to) a hydroxyl group in the 7-position thereof.

(I)

By the way, in the formulas (I), (II), and (III), R represents a lower alkyl group. The lower alkyl group is preferably an alkyl group having 1 to 3 carbon atoms, more preferably an alkyl group having 2 to 3 carbon atoms, further preferably an alkyl group having 2 carbon atoms (ethyl group).

The 2-alkoxy-7-methoxychroman obtained by this process is easily converted into 2-hydroxy-7-methoxychroman by a generally known acid hydrolysis reaction or the like. N-[N-[3-(2-hydroxy-4-methoxyphenyl)propyl]-L-α-aspartyl]-L-phenylalanine 1-methyl ester, a sweetener having a high degree of sweetness, can easily be formed by reacting the 2-hydroxy-7-methoxychroman with aspartame (by reductive alkylation reaction or the like).

The compound obtained herein, the 2-alkoxy-7-methoxychroman (provided the carbon number of the alkoxy group is 2 to 3) is a novel compound, and important as a desired production intermediate. In view of the yield and the cost, 2-ethoxy-7-methoxychroman is especially excellent as a production intermediate.

Although the present process is a process for producing 2-alkoxy-7-methoxychroman, the process is described below in more detail in the context of 2-ethoxy-7-methoxychroman as a typical example. However, it is described as a preferable example, and the present invention is not limited thereto unless the gist of the invention is deviated from.

The formation (synthesis) of 2-ethoxy-7-hydroxychroman in the first step may be carried out by a known process (see Japanese Patent Kokai Publication JP-A-63-203,677, which is incorporated herein by reference). That is, 2-ethoxy-7-hydroxychroman can easily be obtained by reacting resorcinol with acrolein diethyl acetal, preferably in an organic solvent in the presence of an acid catalyst. It is already known that the use of acrolein diethyl acetal provides a high reaction yield in comparison with that of acrolein dimethyl acetal.

It is preferable to use a solvent inactive to the reaction. For example, a reaction solvent described in the known method (see Japanese Patent Kokai Publication JP-A-63-203,677) may be used. In addition, ethers such as diethyl ether, tetrahydrofuran, and the like, esters such as ethyl acetate, butyl acetate, and the like, ketones such as acetone, 2-butanone, and the like, and nitrites such as acetonitrile and the like may also be used.

As the acid catalyst, it is advisable to employ those known as an acid catalyst. Preferably, the acid catalysts described in the known process (see Japanese Patent Kokai Publication JP-A-63-203,677) can be used.

After the completion of the reaction, the resulting reaction solution is alkalized by adding thereto an alkaline aqueous solution, and then extracted with an organic solvent which exhibits a low solubility for alkali salts of resorcinol, for example, aromatic hydrocarbons such as benzene, toluene, and the like, aliphatic hydrocarbons such as hexane, heptane, and the like and halogenated hydrocarbons such as chloroform, carbon tetrachloride, and the like, whereby an organic layer free from unreacted resorcinol can be obtained. The pH value in the extraction is preferably approximately 9. When the pH value is too high, the desired product remains in the aqueous layer and the yield is decreased. Furthermore, it is also possible to recover unreacted resorcinol from another aqueous layer according to a conventional method such as extraction, distillation, column chromatography and the like. The use of this method is more advantageous industrially.

It is advisable to conduct the methylation reaction to the hydroxyl group of 2-ethoxy-7-hydroxychroman obtained in the first stage using a known method for alkylating a phenolic hydroxyl group. For example, the 7-methoxy product can easily be obtained by the reaction of the corresponding 7-hydroxy compound with dimethyl sulfate in the presence of an alkali. The amounts of alkali and dimethyl sulfate used can be at least equimolar amounts based on the 2-ethoxy-7-hydroxychroman. Preferably, the alkali and dimethyl sulfate are used in amounts of 1 to 5 moles per mole of 2-ethoxy-7-hydroxychroman. Examples of the alkali used include hydroxides such as sodium hydroxide, potassium hydroxide, and the like, and carbonates such as sodium carbonate and the like.

When the alkali used is a hydroxide, the reaction solvent (in the case of using a reaction solvent) is not particularly limited so long as the solvent (either a single solvent or a mixed solvent of plural types thereof can be used) does not interfere with the reaction. Water or an alcohol aqueous solution can be used. Further, with respect to the reaction temperature, a temperature range of 0 to 100° C. or so is sufficient. The reaction time varies with the reaction temperature and the other conditions. It is usually in the range of 0.5 to 48 hours or so.

Although unreacted substance(s) such as resorcinol and the like and reaction byproduct(s) are contained in the reaction treatment residue in the first stage, their presence is no particular influence. However, since the methylation reaction in the presence of unreacted resorcinol requires the use of additional alkali and dimethyl sulfate in the amounts of 2 to 10 molar times that of the resorcinol, it is advantageous that unreacted resorcinol is recovered as described above and reused as a starting material of this process. After the completion of the reaction, the desired 2-ethoxy-7-methoxychroman can be obtained by any conventional method(s) such as extraction, distillation, column chromatography, and the like.

By the way, as shown below (in the formula, R represents a lower alkyl group), a process comprising reacting a 2-methoxyphenol with a methoxyallene (IV) and then heating the mixture (see *J. Org. Chem.*, vol. 47, p. 946 (1982), which is incorporated herein by reference) is reported as producing a 2-alkoxy-substituted-methoxychroman. However, this process yields 2,8-dimethoxychroman in a low yield of approximately only 25%.

-continued

In the reaction of the corresponding 3-methoxyphenol with methoxyallene or its equivalent, an acrolein dialkyl acetal for actually obtaining the desired 2-alkoxy-7-methoxychroman according to this process, the product is obtained in a low yield of approximately 30%, and the 3-methoxyphenol is quite costly. Thus, this process is can hardly be said to be an industrially advantageous process.

The 2-alkoxy-7-methoxychroman produced in the process according to the present invention as stated above is easily converted into the 2-hydroxy-7-methoxychroman as stated above, and the 2-hydroxy-7-methoxychroman is then reacted with aspartame, whereby N-[N-[3-(2-hydroxy-4-methoxyphenyl)propyl]-L-α-aspartyl]-L-phenylalanine 1-methyl ester, a sweetener having a high degree of sweetness can easily be formed (synthesized).

The reaction conditions for the conversion of the 2-alkoxy-7-methoxychroman to the 2-hydroxy-7-methoxychroman are not particularly difficult. For example, the conversion of the above-obtained 2-ethoxy-7-methoxychroman to the 2-hydroxy-7-methoxychroman is easily conducted by a generally known acid hydrolysis reaction. Examples of suitable acid catalysts to be used can include mineral acids such as hydrochloric acid, sulfuric acid, perchloric acid, and the like, and organic acids such as methanesulfonic acid, toluenesulfonic acid, and the like. Of these acid catalysts, hydrochloric acid and sulfuric acid which are advantageous industrially are preferable. The reaction solvent is not particularly limited so long as it does not interfere with the reaction. Acetonitrile, acetone, tetrahydrofuran, and the like or hydrous solvent(s) thereof are preferable. The concentration of the substrate (base substance) in the reaction solution is in the range of usually 1 to 100 g or so, preferably 20 to 80 g or so, per 1 liter thereof. The concentration of the acid catalyst is in the range of usually 0.01 to 5 mols or so, preferably 0.1 to 2 mols or so, per 1 liter thereof. The reaction temperature is usually in the range of 0 to 100° C. or so. The reaction time varies with the concentration of the acid catalyst, the reaction temperature and the other conditions. It is usually in the range of 0.5 to 48 hours or so. However, the shorter time is better. After the completion of the reaction, the desired 2-hydroxy-7-methoxychroman can be obtained through the treatment by ordinary method(s) such as extraction, distillation, column chromatography, and the like.

Further, regarding the reaction with aspartame, N-[N-[3-(2-hydroxy-4-methoxyphenyl)propyl]-L-α-aspartyl]-L-phenylalanine 1-methyl ester can be easily obtained with good efficiency by the process for producing an aspartame derivative according to the present invention.

Consequently, according to the process for producing a production intermediate in the present invention, the 2-alkoxy-7-methoxychromans are found to be excellent as production intermediates of the sweeteners and the like. There are also provided an industrially excellent process and the novel dialkoxychroman derivatives which are especially preferable and important as production intermediates, as well as the process for producing the same directed to the sweetener(s) described above.

Incidentally, as a process for obtaining the 2-hydroxy-7-methoxychroman, another route as described below is also known, but it is quite problematic industrially in comparison with the process of the present invention.

That is, a process in which dihydrocoumarin is reduced with diisobutylaluminum hydride (see *J. Org. Chem.*, vol. 54, p. 3282 (1989), which is incorporated herein by reference) is known. However, this reduction reaction is conducted at quite a low temperature. On an industrial scale, a huge plant and equipment investment is required, and besides diisobutylaluminum hydride is quite costly. Thus, it can hardly be said to be an industrially effective process.

Other features of the invention will become apparent in the course of the following descriptions of exemplary embodiments, which are given for illustration of the invention and are not intended to be limiting thereof.

EXAMPLES

Reference Example 1

Synthesis of 2-hydroxy-7-methoxychroman

3-Methoxyphenol (12.4 g, 100 mmol) was added to 100 ml of dichloromethane, and this solution was cooled to 3° C. or less in an ice bath. Subsequently, 0.210 g (1.16 mmol) of p-toluenesulfonic acid monohydrate was added thereto so as to maintain the temperature of the solution at 3° C. or less, and 14.3 g (110 mmol) of acrolein diethyl acetal was further added thereto dropwise over a period of 40 minutes. After the completion of the dropwise addition, the reaction solution was stirred for 2 hours and 20 minutes for reaction while maintaining the reaction solution at 10° C. or less.

After the completion of the reaction, the reaction solution was extracted by adding thereto 50 ml of a saturated aqueous solution of sodium bicarbonate to obtain an organic layer. Further, the aqueous layer was re-extracted by adding thereto 50 ml of dichloromethane, and the dichloromethane layer was combined with the organic layer obtained earlier. The organic layer was washed with 50 ml of a saturated aqueous solution of sodium chloride, and dried over anhydrous magnesium sulfate. Magnesium sulfate was then removed by filtration, and the filtrate was vacuum-concentrated to obtain 21.0 g of oil. This oil was purified by silica gel column chromatography (eluent: toluene), and a fraction containing a desired compound was concentrated to obtain 6.73 g (32.3 mmol) of 2-ethoxy-7-methoxychroman as colorless oil. To 5.50 g (26.4 mmol) of the resulting 2-ethoxy-7-methoxychroman were added 94 ml of acetonitrile, 33 ml of water and 5.8 ml (65.6 mmol) of 35% hydrochloric acid aqueous solution, and the reaction was conducted with stirring at 60° C. for 1 hour. After the completion of the reaction, the reaction solution was extracted by adding thereto 50 ml of water and 200 ml of diethyl ether to obtain an organic layer.

Further, the aqueous layer was re-extracted by adding thereto 100 ml of diethyl ether, and the thus obtained ether layer was combined with the organic layer obtained earlier. The organic layer was washed twice with 100 ml of a saturated aqueous solution of sodium bicarbonate and then with 100 ml of a saturated aqueous solution of sodium chloride, and dried over anhydrous magnesium sulfate. Magnesium sulfate was then removed by filtration, and the filtrate was vacuum-concentrated to obtain 4.77 g of oil. This oil was purified by silica gel column chromatography (eluent: hexane/ethyl acetate=4/1), and a fraction containing a desired compound was concentrated to obtain 3.49 g (19.4 mmol) of 2-hydroxy-7-methoxychroman (racemic compound of 3,4-dihydro-7-methoxy-2H-1-benzopyran-2-ol) as pale-yellow oil.

Reference Example 2

Synthesis of 7-benzyloxy-2-hydroxychroman

Resorcinol (11.0 g, 100 mmol) was added to 100 ml of diethyl ether, and this solution was cooled to 3° C. or less in an ice bath. Subsequently, 0.230 g (1.21 mmol) of p-toluenesulfonic acid monohydrate was added thereto so as to maintain the temperature of the solution at 3° C. or less, and 13 ml (110 mmol) of acrolein dimethyl acetal was further added thereto dropwise over a period of 35 minutes. After the completion of the dropwise addition, the reaction solution was reacted with stirring for 4 hours while maintaining the reaction solution at 10° C. or less. After the completion of the reaction, the reaction solution was extracted by adding thereto 50 ml of a saturated aqueous solution of sodium bicarbonate to obtain an organic layer. Further, the aqueous layer was re-extracted by adding thereto 50 ml of diethyl ether, and the thus obtained ether layer was combined with the organic layer obtained earlier. The organic layer was washed with 100 ml of a saturated aqueous solution of sodium chloride, and dried over anhydrous magnesium sulfate. Magnesium sulfate was then removed by filtration, and the filtrate was vacuum-concentrated to obtain 19.1 g of oil.

The resulting oil was purified by silica gel column chromatography (eluent: hexane/ethyl acetate=4/1), and a fraction containing a desired compound was concentrated to obtain 7.72 g (42.8 mmol) of 7-hydroxy-2-methoxychroman as colorless oil. To 7.72 g (42.8 mmol) of the resulting 7-hydroxy-2-methoxychroman were added 45 ml of dimethylformamide, 13.7 g (99.2 mmol) of anhydrous potassium carbonate and 8.3 ml (70.3 mmol) of benzyl bromide, and the reaction was conducted overnight at room temperature with stirring. After the completion of the reaction, the reaction solution was extracted by adding thereto 200 ml of water and 200 ml of ethyl acetate to obtain an organic layer. Further, the aqueous layer was re-extracted in the same manner twice by adding thereto 100 ml of ethyl acetate, and the thus obtained ethyl acetate layer was combined with the organic layer obtained earlier. The organic layer was washed four times with 150 ml of water, and dried over anhydrous magnesium sulfate. Magnesium sulfate was then removed by filtration, and the filtrate was vacuum-concentrated to obtain 14.6 g of oil. This oil was purified by silica gel column chromatography (eluent: hexane/ethyl acetate=12/1), and a fraction containing a desired compound was concentrated to obtain 11.3 g (41.6 mmol) of 7-benzyloxy-2-methoxychroman as colorless oil.

To 10.2 g (37.5 mmol) of the thus-obtained 7-benzyloxy-2-methoxychroman were added 130 ml of tetrahydrofuran, 40 ml of water and 12 ml (71.7 mmol) of a 60% perchloric acid aqueous solution, and the reaction was conducted with stirring at 60° C. for 4 hours. After the completion of the reaction, the reaction solution was extracted by adding thereto 150 ml of water and 300 ml of diethyl ether to obtain an organic layer. Further, the aqueous layer was re-extracted by adding thereto 300 ml of diethyl ether, and the thus obtained ether layer was combined with the organic layer obtained earlier. The organic layer was washed twice with 150 ml of a saturated aqueous solution of sodium bicarbonate and then with 150 ml of a saturated aqueous solution of sodium chloride, and dried over anhydrous magnesium sulfate. Magnesium sulfate was then removed by filtration, and the filtrate was vacuum-concentrated to obtain 10.0 g of oil. This oil was purified by silica gel column chromatography (eluent: hexane/ethyl acetate=5/1), and a fraction containing a desired compound was concentrated to obtain 6.32 g (24.7 mmol) of 7-benzyloxy-2-hydroxychroman as colorless oil.

Reference Example 3

Synthesis of 2-hydroxy-7-methylchroman

Diethyl ether (490 ml) was added to 61.0 g (564 mmol) of m-cresol, and this solution was cooled to 5° C. or less in an ice bath. Subsequently, 1.07 g (5.64 mmol) of p-toluenesulfonic acid monohydrate was added so as to maintain the temperature of the solution at 5° C. or less, and 95 ml (620 mmol) of acrolein diethyl acetal was further added dropwise over a period of 80 minutes. After the completion of the dropwise addition, the reaction solution was reacted with stirring for 1 hour and 10 minutes while maintaining the reaction solution at 5° C. or less. After the completion of the reaction, the reaction solution was extracted by adding thereto 100 ml of diethyl ether and 250 ml of a 1M sodium hydroxide aqueous solution in two divided portions to obtain an organic layer. Further, the aqueous layer was re-extracted by adding thereto 400 ml of diethyl ether, and the thus obtained ether layer was combined with the organic layer obtained earlier. The organic layer was washed with 500 ml of a saturated aqueous solution of sodium chloride, and dried over anhydrous magnesium sulfate. Magnesium sulfate was then removed by filtration, and the filtrate was vacuum-concentrated to obtain 52.9 g of oil.

The resulting oil was purified by silica gel column chromatography (eluent: hexane/ethyl acetate=19/1), and a fraction containing a desired compound was concentrated to obtain 4.64 g (24.1 mmol) of 2-ethoxy-7-methylchroman as pale-yellow oil. To 4.59 g (23.9 mmol) of the resulting 2-ethoxy-7-methylchroman were added 75 ml of acetonitrile, 25 ml of water and 5.3 ml (60.0 mmol) of a 35% hydrochloric acid aqueous solution, and the reaction was conducted at 60° C. for 1 hour with stirring. After the completion of the reaction, the reaction solution was extracted by adding thereto 50 ml of water and 200 ml of diethyl ether to obtain an organic layer. Further, the aqueous layer was re-extracted by adding thereto 100 ml of diethyl ether, and the thus obtained ether layer was combined with the organic layer obtained earlier. The organic layer was washed twice with 100 ml of a saturated aqueous solution of sodium bicarbonate and then with 100 ml of a saturated aqueous solution of sodium chloride, and dried over anhydrous magnesium sulfate. Magnesium sulfate was then removed by filtration, and the filtrate was vacuum-concentrated to obtain 3.90 g of oil. This oil was homogenized by adding thereto 0.5 ml of ethyl acetate and 10 ml of hexane at 60° C., and cooled to 5° C. for crystallization to precipitate crystals. Further, the mother liquor was vacuum-concentrated, and then purified by silica gel column chromatography (eluent: hexane/ethyl acetate=7/1), and a fraction containing a desired compound was concentrated. This concentrated solution was homogenized by adding thereto 15 ml of hexane, and cooled to 5° C. for crystallization to precipitate crystals. These crystals were collected by filtration, and vacuum-dried at room temperature for 7 hours to obtain 2.68 g (16.3 mmol) of 2-hydroxy-7-methylchroman.

Example 1

Synthesis of N-[N-[3-(2-hydroxy-4-methoxyphenyl)propyl]-L-α-aspartyl]-L-phenylalanine 1-methyl ester (1)

2-Hydroxy-7-methoxychroman (0.870 g, 4.83 mmol) and 1.50 g (5.10 mmol) of aspartame were added to a mixed solvent (50 ml) of methanol and water (mixing ratio 3:2 v/v), and stirred at a temperature of 45° C. for a while for dissolution. To this solution was added 0.520 g of 10% palladium carbon (water content 50%), and the reaction was conducted with stirring in a hydrogen atmosphere of normal pressure (0.1 MPa) at 45° C. for 48 hours. The reaction solution was filtered to remove the catalyst, and quantitative determination was conducted by the high-performance liquid chromatography (HPLC). It was then found that 1.33 g (2.90 mmol, 60%) of N-[N-[3-(2-hydroxy-4-methoxyphenyl)propyl]-L-α-aspartyl]-L-phenylalanine 1-methyl ester was formed.

Example 2

Synthesis of N-[N-[3-(2-hydroxy-4-methoxyphenyl)propyl]-L-α-aspartyl]-L-phenylalanine 1-methyl ester (2)

The reaction was conducted in the same manner as in Example 1 except that a mixed solvent of methanol and water (mixing ratio 4:1 v/v) was used instead of the mixed solvent of methanol and water (mixing ratio 3:2 v/v). The reaction solution was filtered to remove the catalyst, and quantitative determination was conducted by HPLC. It was then found that 1.42 g (3.10 mmol, 64%) of N-[N-[3-(2-hydroxy-4-methoxyphenyl)propyl]-L-α-aspartyl]-L-phenylalanine 1-methyl ester was formed.

Example 3

Synthesis of N-[N-[3-(2-hydroxy-4-methoxyphenyl)propyl]-L-α-aspartyl]-L-phenylalanine 1-methyl ester (3)

The reaction was conducted in the same manner as in Example 1 except that methanol was used instead of the mixed solvent of methanol and water (mixing ratio 3:2 v/v) and the reaction time was 18 hours. The reaction solution was filtered to remove the catalyst, and quantitative determination was conducted by HPLC. It was then found that 1.22 g (2.66 mmol, 55%) of N-[N-[3-(2-hydroxy-4-methoxyphenyl)propyl]-L-α-aspartyl]-L-phenylalanine 1-methyl ester was formed.

Example 4

Synthesis of N-[N-[3-(2-hydroxy-4-methoxyphenyl)propyl]-L-α-aspartyl]-L-phenylalanine 1-methyl ester (4)

The reaction was conducted in the same manner as in Example 2 except that 0.11 ml of acetic acid was used in combination and the reaction time was 24 hours. The reaction solution was filtered to remove the catalyst, and quantitative determination was conducted by HPLC. It was then found that 1.59 g (3.47 mmol, 72%) of N-[N-[3-(2-hydroxy-4-methoxyphenyl)propyl]-L-α-aspartyl]-L-phenylalanine 1-methyl ester was formed.

Example 5

Synthesis of N-[N-[3-(2-hydroxy-4-methoxyphenyl)propyl]-L-α-aspartyl]-L-phenylalanine 1-methyl ester (5)

The reaction was conducted in the same manner as in Example 2 except that 2.14 g (7.27 mmol) of aspartame was used and the reaction time was 24 hours. The reaction solution was filtered to remove the catalyst, and quantitative determination was conducted by HPLC. It was then found that 1.68 g (3.67 mmol, 76%) of N-[N-[3-(2-hydroxy-4-methoxyphenyl)propyl]-L-α-aspartyl]-L-phenylalanine 1-methyl ester was formed.

Example 6

Synthesis of N-[N-[3-(2-hydroxy-4-methoxyphenyl propyl]-L-α-aspartyl]-L-phenylalanine 1-methyl ester (6)

2-Hydroxy-7-methoxychroman (0.580 g, 3.22 mmol) and 1.00 g (3.40 mmol) of aspartame were added to a mixed solvent (33 ml) of methanol and water (mixing ratio 3:2 v/v), and stirred at a temperature of 35° C. for a time to achieve dissolution. To this solution was added 0.330 g of 10% palladium carbon (water content 50%), and the reaction was conducted with stirring in a hydrogen atmosphere of normal pressure (0.1 MPa) at 35° C. for 70 hours. The reaction solution was heated to 60° C., and the catalyst was removed by filtration, and further washed with 10 ml of methanol. The filtrate and washings (the wash solution) were combined, and quantitative determination was conducted by HPLC therefor. It was then found that 0.992 g (2.16 mmol, 67%) of N-[N-[3-(2-hydroxy-4-methoxyphenyl)propyl]-L-α-aspartyl]-L-phenylalanine 1-methyl ester was formed.

Example 7

Synthesis of N-[N-[3-(2,4-dihydroxyphenyl)propyl]-L-α-aspartyl]-L-phenylalanine 1-methyl ester 7-Benzyloxy-2-hydroxychroman (0.950 g, 3.71 mmol) and 1.15 g (3.90 mmol) of aspartame were added to a mixed solvent (40 ml) of methanol and water (mixing ratio 3:2 v/v), and stirred at a temperature of 40° C. for a while. To this slurry was added 0.40 g of 10% palladium carbon (water content 50%), and the reaction was conducted with stirring in a hydrogen atmosphere of normal pressure (0.1 MPa) at 40° C. for 48 hours. The reaction solution was filtered to remove the catalyst, and the residue was vacuum-concentrated to dryness. This dry solid was subjected to a quantitative determination by $^1$H-NMR (DMSO-$d_6$, 300 MHz, inner standard substance: 1,1,2,2-tetrachloroethane). It was then found that 1.37 g (3.08 mmol, 83%) of N-[N-[3-(2,4-dihydroxyphenyl)propyl]-L-α-aspartyl]-L-phenylalanine 1-methyl ester was formed.

Example 8

Synthesis of N-[N-[3-(2-hydroxy-4-methylphenyl)propyl]-L-α-aspartyl]-L-phenylalanine 1-methyl ester 2-Hydroxy-7-methylchroman (2.50 g, 15.2 mmol) and 4.71 g (16.0 mmol) of aspartame were added to 155 ml of a mixed solvent of methanol and water (mixing ratio 4:1 v/v), and stirred at a temperature of 45° C. for a time to effect dissolution. To this solution was added 1.41 g of 10% palladium carbon (water content 50%), and the reaction was conducted with stirring in a hydrogen atmosphere of normal pressure (0.1 MPa) at 45° C. for 24 hours. The reaction solution was filtered to remove the catalyst, and the catalyst was further washed with 10 ml of methanol. The filtrate and washings were combined, and quantitative determination was conducted by HPLC therefor. It was then found that 3.84 g (8.68 mmol, 57%) of N-[N-[3-(2-hydroxy-4-methylphenyl)propyl]-L-α-aspartyl]-L-phenylalanine 1-methyl ester was formed.

Example 9

Purification of N-[N-[3-(2-hydroxy-4-methoxyphenyl)propyl]-L-α-aspartyl]-L-phenylalanine 1-methyl ester and separation of its crystals (1)

Ten milliliters were taken from the 47 ml reaction solution containing N-[N-[3-(2-hydroxy-4-methoxyphenyl)propyl]-L-α-aspartyl]-L-phenylalanine 1-methyl ester (1.22 g, 2.66 mmol) as obtained in Example 3 was used, and 40 ml of ethyl acetate was added to the reaction solution (10 ml), and stirred at room temperature to precipitate crystals. After stirring was conducted at the same temperature for 4 hours, the crystals were separated by filtration, washed with a small amount of ethyl acetate, and vacuum-dried overnight at room temperature to obtain 0.188 g (0.410 mmol, crystallization yield 72%) of N-[N-[3-(2-hydroxy-4-methoxyphenyl)propyl]-L-α-aspartyl]-L-phenylalanine 1-methyl ester.

The purity measured by the high-performance liquid chromatography (HPLC) was 96% or more.

Example 10

Purification of N-[N-[3-(2-hydroxy-4-methoxyphenyl)propyl]-L-α-aspartyl]-L-phenylalanine 1-methyl ester and separation of its crystals (2)

Twenty milliliters were taken from the 42 ml reaction solution containing N-[N-[3-(2-hydroxy-4-methoxyphenyl)propyl]-L-α-aspartyl]-L-phenylalanine 1-methyl ester (1.42 g, 3.10 mmol) as obtained in Example 2 was used, and the reaction solution (20 ml) was vacuum-concentrated at 45° C. to remove methanol. Then, 22 ml of acetone was added thereto, and the mixture was stirred at room temperature to precipitate crystals. After stirring was conducted at the same temperature for 4 hours, the crystals were separated by filtration, washed with 12 ml of acetone, and vacuum-dried overnight at room temperature to obtain 0.337 g (0.735 mmol, crystallization yield 50%) of N-[N-[3-(2-hydroxy-4-methoxyphenyl)propyl]-L-α-aspartyl]-L-phenylalanine 1-methyl ester. The purity measured by HPLC was 97% or more.

Example 11

Purification of N-[N-[3-(2-hydroxy-4-methoxyphenyl)propyl]-L-α-aspartyl]-L-phenylalanine 1-methyl ester and separation of its crystals (3)

Forty-one milliliters were taken from the 52 ml reaction solution containing N-[N-[3-(2-hydroxy-4-methoxyphenyl)propyl]-L-α-aspartyl]-L-phenylalanine 1-methyl ester (1.59 g, 3.47 mmol) as obtained in Example 4 was used, and 68 ml of water was added to the reaction solution (41 ml) at room temperature. Since crystals were partially precipitated by this procedure, heating was conducted at 50° C. to form a homogeneous solution. The solution was then cooled to 10° C. while being stirred to precipitate crystals. After stirring was conducted at the same temperature for 4 hours, the crystals were separated by filtration, washed with a small amount of water, and vacuum-dried overnight at room temperature to obtain 1.20 g of coarse crystals (content of a desired compound 1.05 g, crystallization yield 84%). To 1.10 g of the resulting coarse crystals was added 22 ml of a mixed solvent of acetone and water (mixing ratio 4:1 v/v) for dissolution at 60° C., and the mixture was cooled to 5° C. (cooling rate 15° C./hr) while being stirred to precipitate the crystals. After the mixture was allowed to stand at the same temperature for 3 days, the crystals were separated by filtration, washed with a small amount of a mixed solvent of acetone and water (mixing ratio 4:1 v/v), and vacuum-dried at room temperature for 2.5 hours to obtain 0.600 g (1.31 mmol, crystallization yield 62%) of N-[N-[3-(2-hydroxy-4-methoxyphenyl)propyl]-L-α-aspartyl]-L-phenylalanine 1-methyl ester. The purity measured by HPLC was 98% or more.

Example 12

Purification of N-[N-[3-(2-hydroxy-4-methoxyphenyl)propyl]-L-α-aspartyl]-L-phenylalanine 1-methyl ester and separation of its crystals (4)

The reaction was conducted in the same manner as in Example 4 except that the reaction temperature was 35° C. The reaction solution was filtered to remove the catalyst, and the catalyst was further washed with 5 ml of methanol. The filtrate and washings were combined to obtain 49 ml of a reaction solution containing 1.39 g (3.03 mmol) of N-[N-[3-(2-hydroxy-4-methoxyphenyl)propyl]-L-α-aspartyl]-L-phenylalanine 1-methyl ester. This reaction solution (42 ml) was vacuum-concentrated at 50° C. to remove methanol, and 4 ml of isopropyl alcohol was then added thereto. After the mixture was heated at 85° C., 7.7 ml of water was further added thereto, and the resulting solution was cooled to 10° C. while being stirred to precipitate crystals. After stirring was conducted overnight at the same temperature, the crystals were separated by filtration, washed with 15 ml of water, and vacuum-dried at 45° C. for 3 hours to obtain 1.18 g (2.58 mmol, crystallization yield 99%) of N-[N-[3-(2-hydroxy-4-methoxyphenyl)propyl]-L-α-aspartyl]-L-phenylalanine 1-methyl ester. The purity measured by HPLC was 98% or more.

Example 13

Purification of N-[N-[3-(2-hydroxy-4-methoxyphenyl)propyl]-L-α-aspartyl]-L-phenylalanine 1-methyl ester and separation of its crystals (5)

To 1.06 g (2.31 mmol) of the crystals obtained in Example 12 was added 50 ml of a mixed solvent of isopropyl alcohol and water (mixing ratio 9:1 v/v), and they were dissolved at 75° C. Cooling was conducted to 5° C. (cooling rate 10° C./hr) with stirring to precipitate crystals. After stirring was conducted overnight at the same temperature, the crystals were separated by filtration, washed with a small amount of isopropyl alcohol, and vacuum-dried at 40° C. for 3.5 hours to obtain 0.831 g (1.81 mmol, crystallization yield 78%) of N-[N-[3-(2-hydroxy-4-methoxyphenyl)propyl]-L-α-aspartyl]-L-phenylalanine 1-methyl ester. The purity measured by HPLC was 99% or more.

Example 14

Purification of N-[N-[3-(2-hydroxy-4-methoxyphenyl)propyl]-L-α-aspartyl]-L-phenylalanine 1-methyl ester and separation of its crystals (6)

2-Hydroxy-7-methoxychroman (4.37 g, 24.3 mmol) and 7.52 g (25.6 mmol) of aspartame were added to 250 ml of a mixed solvent of methanol and water (mixing ratio 3:2 v/v), and the mixture was stirred at a temperature of 40° C. for a while to effect dissolution. To this solution was added 2.56 g of 10% palladium carbon (water content 50%), and the reaction was conducted with stirring in a hydrogen atmosphere of normal pressure (0.1 MPa) at 40° C. for 48 hours. The reaction solution was filtered to remove the catalyst, and the catalyst was further washed with 40 ml of methanol. The filtrate and washings (the wash solution) were combined, and vacuum-concentrated to remove 60 ml of methanol. Then, the residue was cooled to 10° C. to precipitate crystals. After the residue was allowed to stand overnight at the same temperature, the crystals were then separated by filtration, washed with a small amount of water, and vacuum-dried at 40° C. for 3 hours to obtain 7.75 g (16.9 mmol, crystallization yield 66%) of N-[N-[3-(2-hydroxy-4-methoxyphenyl)propyl]-L-α-aspartyl]-L-phenylalanine 1-methyl ester. The purity measured by HPLC was 95% or more.

Example 15

Purification of N-[N-[3-(2-hydroxy-4-methoxyphenyl)propyl]-L-α-aspartyl]-L-phenylalanine 1-methyl ester and separation of its crystals (7)

To 1.00 g (2.31 mmol) of the crystals obtained in Example 14 was added 60 ml of a mixed solvent of methanol and water (mixing ratio 3:2 v/v), and they were dissolved at 60° C. Cooling was conducted to 5° C. to precipitate the crystals. After the solution was allowed to stand overnight at the same temperature, the crystals were separated by filtration, washed with a small amount of water, and vacuum-dried at 40° C. for 11 hours to obtain 0.682 g (1.49 mmol, crystallization yield 68%) of N-[N-[3-(2-hydroxy-4-methoxyphenyl)propyl]-L-α-aspartyl]-L-phenylalanine 1-methyl ester. The purity measured by HPLC was 99% or more.

Example 16

Purification of N-[N-[3-(2-hydroxy-4-methoxyphenyl)propyl]-L-α-aspartyl]-L-phenylalanine 1-methyl ester and separation of its crystals (8)

To 1.07 g (2.19 mmol) of the crystals obtained in Example 14 was added 16 ml of methyl ethyl ketone saturated with water, and they were dissolved at 70° C. Cooling was conducted to 5° C. (cooling rate 10° C./hr) with stirring to precipitate the crystals. After the solution was allowed to stand at the same temperature for 2 days, the crystals were separated by filtration, washed with methyl ethyl ketone saturated with a small amount of water, and vacuum-dried at 40° C. for 2 hours to obtain 0.621 g (1.36 mmol, crystallization yield 58%) of N-[N-[3-(2-hydroxy-4-methoxyphenyl)propyl]-L-α-aspartyl]-L-phenylalanine 1-methyl ester. The purity measured by HPLC was 98% or more.

Example 17

Purification of N-[N-[3-(2,4-dihydroxyphenyl)propyl]-L-α-aspartyl]-L-phenylalanine 1-methyl ester and separation of its crystals (1)

Two milliliters of methanol was added to the dry product containing N-[N-[3-(2,4-dihydroxyphenyl)propyl]-L-α-aspartyl]-L-phenylalanine 1-methyl ester (1.37 g, 3.08 mmol) as obtained in Example 7, and it was dissolved at 60° C. Further, while stirring was conducted at the same temperature, 40 ml of ethyl acetate was added thereto to precipitate the crystals. After the slurry was cooled to 110° C. and allowed to stand overnight, the crystals were separated by filtration, and washed with 5 ml of ethyl acetate to obtain 4.16 g of wet coarse crystals (content of a desired compound 1.24 g, recovery rate 75%). To 4.03 g of the resulting wet coarse crystals was added 12 ml of a mixed solvent of methanol and water (mixing ratio 1:5 v/v), and the slurry was stirred at 60° C. for 1 hour, and cooled to 110° C. to precipitate the dissolved crystals. After the slurry was allowed to stand at the same temperature for 4 days, the crystals were separated by filtration, washed with a small amount of water, and vacuum-dried at 40° C. for 2 hours to obtain 0.789 g (1.78 mmol, crystallization yield 66%) of N-[N-[3-(2,4-dihydroxyphenyl)propyl]-L-α-aspartyl]-L-phenylalanine 1-methyl ester. The purity measured by HPLC was 97% or more.

Example 18

Purification of N-[N-[3-(2,4-dihydroxyphenyl)propyl]-L-α-aspartyl]-L-phenylalanine 1-methyl ester and separation of its crystals (2)

2,7-Dihydroxychroman (0.750 g, 4.51 mmol) and 1.40 g (4.75 mmol) of aspartame were added to 48 ml of a mixed solvent of methanol and water (mixing ratio 3:2 v/v), and the mixture was stirred at a temperature of 40° C. for a while. To this slurry was added 0.470 g of 10% palladium carbon (water content 50%), and the reaction was conducted with stirring in a hydrogen atmosphere of normal pressure (0.1 MPa) at 40° C. for 48 hours. The reaction solution was filtered to remove the catalyst, and vacuum-concentrated to dryness. To this dry product was added 2 ml of methanol, and it was dissolved at 60° C. Further, while stirring was conducted at the same temperature, 40 ml of ethyl acetate was added thereto to precipitate crystals. After this slurry was cooled to 10° C. and allowed to stand overnight, the crystals were separated by filtration, and washed with 5 ml of ethyl acetate to obtain 3.87 g of wet coarse crystals (content of a desired compound 1.60 g, recovery rate 80%). To 3.63 g of the resulting wet coarse crystals was added 12 ml of a mixed solvent of methanol and water (mixing ratio 1:5 v/v), and they were dissolved at 60° C. Cooling was conducted to 10° C. to precipitate the crystals. After the slurry was allowed to stand overnight at the same temperature, the crystals were then separated by filtration, washed with a small amount of water, and vacuum-dried at 40° C. for 11 hours to obtain 1.02 g (2.30 mmol, crystallization yield 68%) of N-[N-[3-(2,4-dihydroxyphenyl)propyl]-L-α-aspartyl]-L-phenylalanine 1-methyl ester. The purity measured by HPLC was 98% or more.

Example 19

Purification of N-[N-[3-(2-hydroxy-4-methylphenyl)propyl]-L-α-aspartyl]-L-phenylalanine 1-methyl ester and separation of its crystals The solution containing 3.84 g (8.68 mmol) of N-[N-[3-(2-hydroxy-4-methylphenyl)propyl]-L-α-aspartyl]-L-phenylalanine 1-methyl ester as obtained in Example 8 was vacuum-concentrated to dryness. To this dry product was added 5 ml of methanol, and it was dissolved at 60° C. Further, while stirring was conducted at the same temperature, 23 ml of ethyl acetate was added thereto to precipitate the crystals. After the slurry was cooled to 5° C. and allowed to stand overnight, the crystals were separated by filtration, and washed with 8 ml of ethyl acetate to obtain 9.73 g of wet coarse crystals (content of a desired compound 3.63 g, recovery rate 54%). To the resulting wet coarse crystals, was added 45 ml of methanol, and they were dissolved at 60° C., and the thus obtained solution was vacuum-concentrated at 40° C. At this time, the amount of the distillate was 27 ml. The resulting concentrated solution was heated to 60° C. Further, while stirring was conducted at the same temperature, 40 ml of water was added thereto to precipitate the crystals. After this slurry was cooled to 5° C. and allowed to stand overnight, the crystals were separated by filtration, washed with 8 ml of water, and vacuum-dried at 40° C. for 4.5 hours to obtain 3.35 g (7.57 mmol, crystallization yield 92%) of N-[N-[3-(2-hydroxy-4-methylphenyl)propyl]-L-α-aspartyl]-L-phenylalanine 1-methyl ester. The purity measured by HPLC was 96% or more.

Example 20

Physical properties of N-[N-[3-(2-hydroxy-4-methoxyphenyl)propyl]-L-α-aspartyl]-L-phenylalanine 1-methyl ester crystals The physical properties of the crystals of the above-referenced compound (title compound) obtained by the present invention are as follows.

Odorless white crystals.

Differential thermal analysis:
  Measurement temperature range: 50 to 300° C.; rate of temperature rise:
  110° C./minute; melting point: 194° C.

Figure 1:
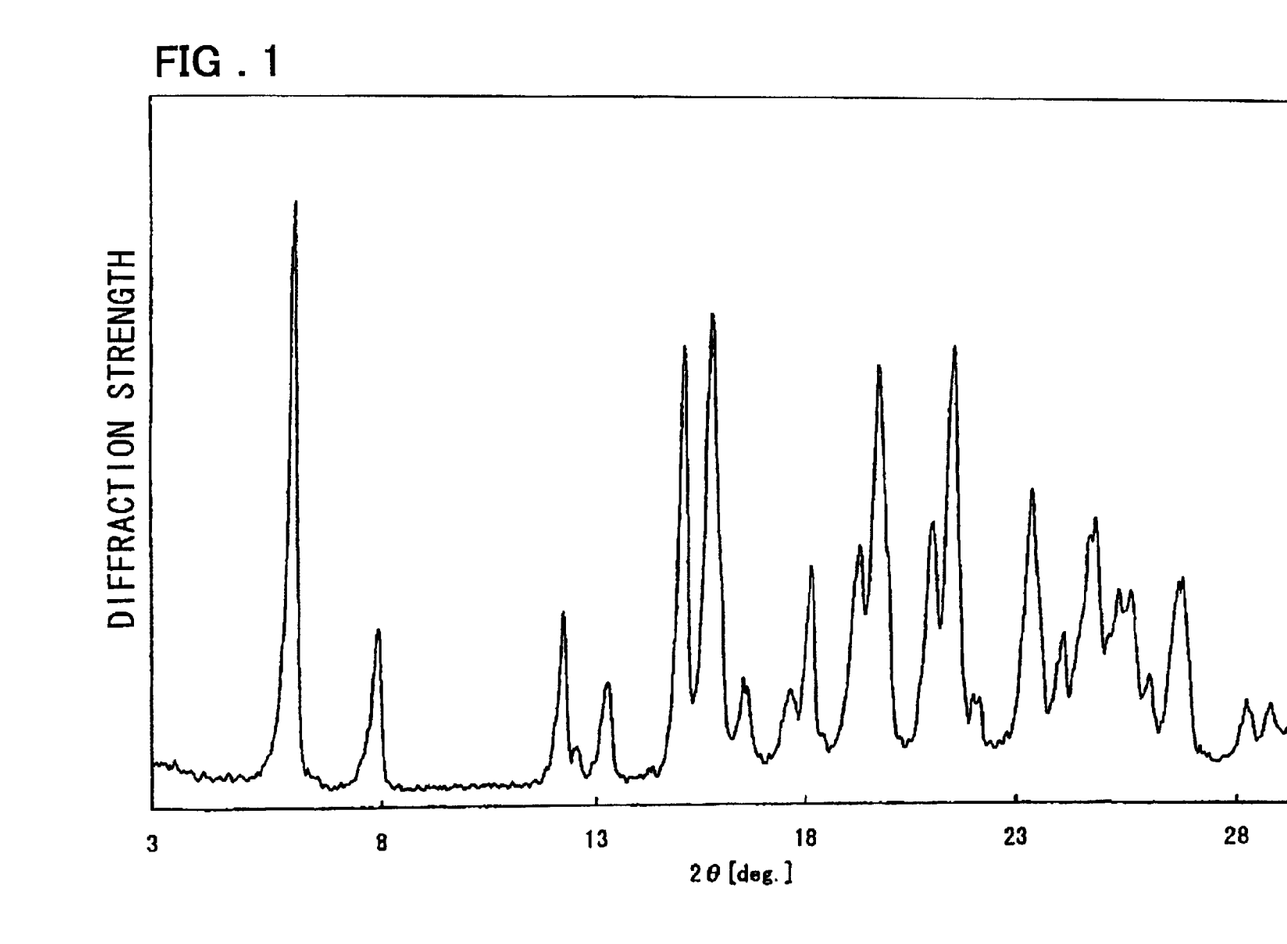
FIG. 1 is a powder X-ray diffraction pattern of N-[N-[3-(2-hydroxy-4-methoxyphenyl)propyl]-L-α-aspartyl]-L-phenylalanine 1-methyl ester crystals.

Powder X-ray diffraction:
  As shown in FIG. 1, characteristic diffraction peaks were shown at diffraction angles (2θ, CuKα rays) of 6.1°, 15.8°, 19.7°, and 21.6°.

Example 21

Physical properties of N-[N-[3-(2,4-dihydroxyphenyl)propyl]-L-α-aspartyl]-L-phenylalanine 1-methyl ester crystals The physical properties of the crystals of the above-referenced compound obtained according to the present invention are as follows.

Odorless white crystals.

Differential thermal analysis:

Measurement temperature range: 50 to 300° C.; rate of temperature rise:

10° C./minute; melting point: 190° C.

Figure 2:
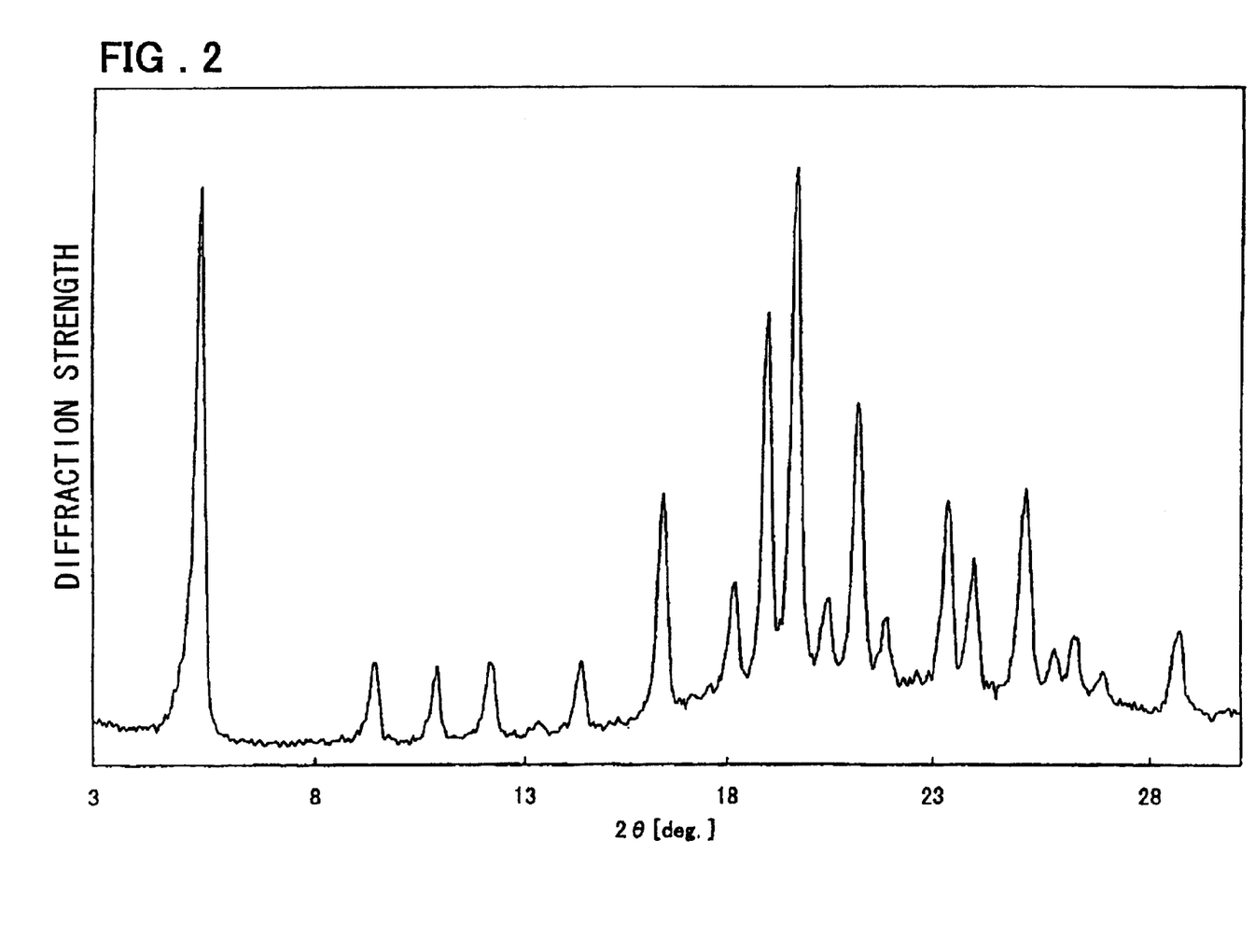
FIG. 2 is a powder X-ray diffraction pattern of N-[N-[3-(2,4-dihydroxyphenyl)propyl]-L-α-aspartyl]-L-phenylalanine 1-methyl ester crystals.

Powder X-ray diffraction:

As shown in FIG. 2, characteristic diffraction peaks were shown at diffraction angles (2 θ, CuKα rays) of 5.5°, 19.0°, 19.7°, and 21.2°.

Example 22

Physical properties of N-[N-[3-(2-hydroxy-4-methylphenyl)propyl]-L-α-aspartyl]-L-phenylalanine 1-methyl ester crystals The physical properties of the crystals of the above-referenced compound obtained by the present invention are as follows.

Odorless white crystals.

Differential thermal analysis:

Measurement temperature range: 50 to 300° C.; rate of temperature rise:

10° C./minute; melting point: 177° C.

Figure 3:
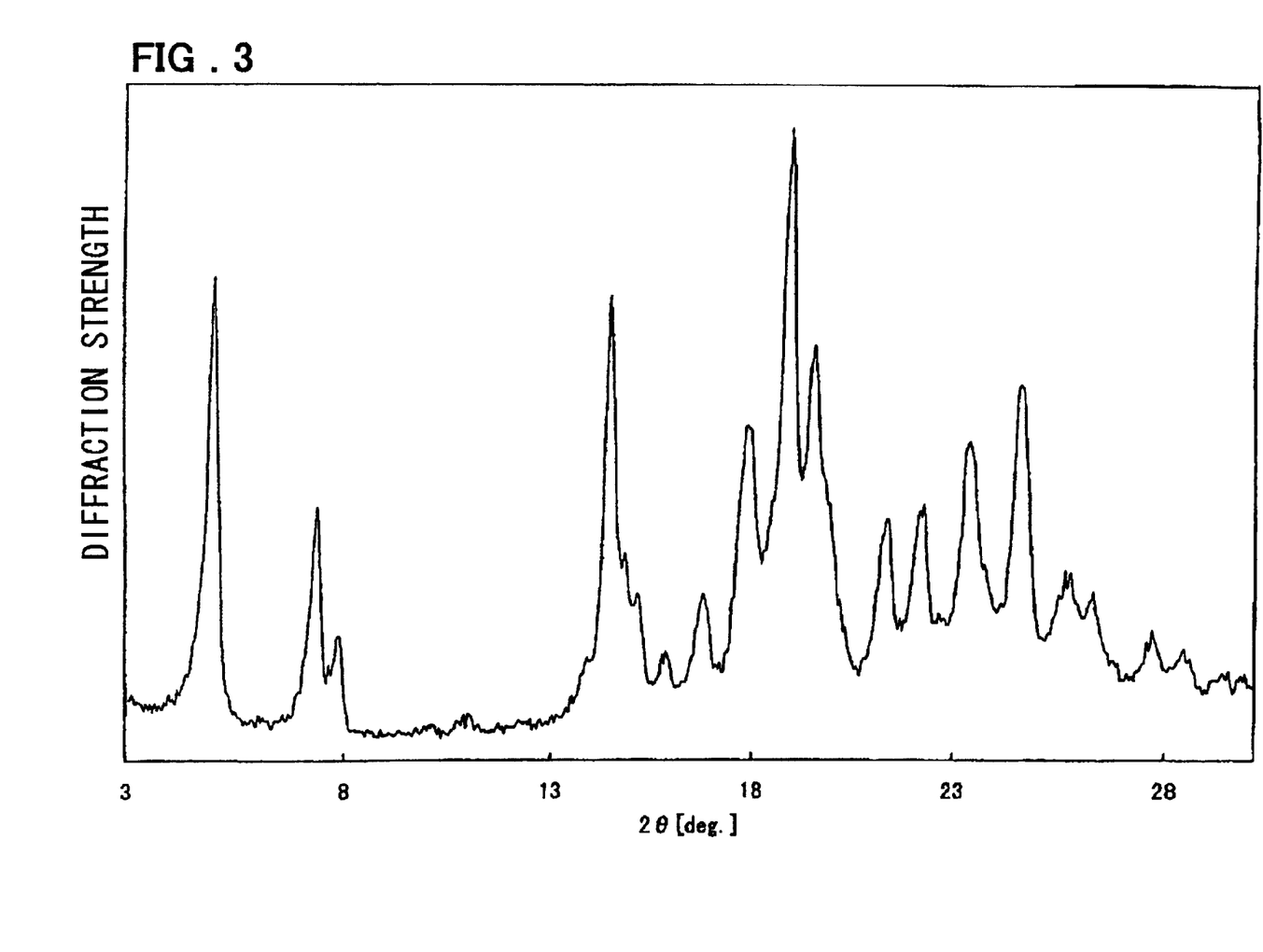
FIG. 3 is a powder X-ray diffraction pattern of N-[N-[3-(2-hydroxy-4-methylphenyl)propyl]-L-α-aspartyl]-L-phenylalanine 1-methyl ester crystals.

Powder X-ray diffraction:

As shown in FIG. 3, characteristic diffraction peaks were shown at diffraction angles (2 θ, CuKα rays) of 5.0°, 14.5°, 19.0°, and 19.6°.

Example 23

Synthesis of 2-ethoxy-7-hydroxychroman

A 500-milliliter (ml) flask fitted with a dropping funnel was charged with 10.0 g of resorcinol, 0.2 g of p-toluenesulfonic acid monohydrate, and 100 ml of acetonitrile for dissolution, and the mixture was cooled with ice. To this solution was slowly added dropwise 11.1 ml of acrolein diethyl acetal under room temperature. After the dropwise addition, the mixture was stirred for 1 hour while being cooled with ice. After 5 ml of a 5% sodium hydroxide aqueous solution and 30 ml of water were added thereto, the acetonitrile was removed by distillation in vacuo (under vacuum pressure), and the residue was extracted three times with 50 ml of chloroform. Subsequently, the chloroform layer obtained was washed with 30 ml of water, the chloroform was then removed by distillation in vacuo, and the resulting residue was purified by distillation to obtain 10.9 g of a colorless liquid (yield 62%).

Example 24

Synthesis of 2-ethoxy-7-methoxychroman

The above-obtained 2-ethoxy-7-hydroxychroman (10.9 g) was dissolved in 60 ml of methanol, and 10.6 g of dimethyl sulfate and 13.5 g of a 25% sodium hydroxide aqueous solution were added thereto at room temperature. The mixture was stirred at this temperature for 1 hour. After 30 ml of water was added thereto, the methanol was removed by distillation in vacuo, and the residue was extracted twice with 50 ml of toluene. The toluene layer was washed with water, and the toluene was removed by distillation in vacuo. The resulting residue was purified by distillation to obtain 11.0 g of a desired colorless liquid (yield 94%).

Boiling point 117 to 118° C./0.2 mm (27 Pa).

$^1$H-NMR spectrum (CDCl$_3$ solvent: ppm)

1.19 (3H, t, J=7.2 Hz), 1.86–2.08 (2H, m), 2.52–2.61 (1H, m), 2.83–2.93 (1H, m), 3.58–3.67 (1H, m), 3.75 (3H, s), 3.84–3.92 (1H, m), 5.20–5.23 (1H, m), 6.39 (1H, m), 6.46 (1H, ddd, J=1.5, 2.7, 9.2 Hz), 6.93 (1H, d, J=9.2 Hz).

Example 25

Synthesis of 7-hydroxy-2-methoxychroman

A 500-milliliter flask fitted with a dropping funnel was charged with 11.0 g of resorcinol, 0.2 g of p-toluenesulfonic acid monohydrate and 100 ml of diethyl ether for dissolution, and the mixture was cooled with ice. To this solution was slowly added dropwise 13.0 ml of acrolein dimethyl acetal under room temperature. After the dropwise addition, the mixture was stirred for 4 hours while being cooled with ice. To this was added 30 ml of water, the solution was weakly alkalized with a 5% sodium hydroxide aqueous solution, and the organic layer was then washed. After the separation of layers in the solution, the aqueous layer was extracted three times with 50 ml of diethyl ether, and thus obtained ether layers were combined with the previous organic layer. The combined layer was washed with 50 ml of water, and diethyl ether was then removed by distillation in vacuo therefrom. The resulting residue was purified by distillation to obtain 7.7 g of a colorless liquid (yield 43%).

The resulting compound was subjected to a reaction of methylating the hydroxyl group at the 7-position thereof in the same manner as in Example 23 to produce a 7-methoxylated compound as well.

Example 26

Synthesis of 2-hydroxy-7-methoxychroman

A 500-milliliter egg plant type flask was charged with 5.14 g of 2-ethoxy-7-methoxychroman, 74 ml of acetonitrile and 25 ml of water, and 4.8 ml of a 35% hydrochloric acid aqueous solution was slowly added thereto dropwise at room temperature. The solution was stirred at 60° C. for 20 minutes, and then cooled to 20° C. The reaction solution was neutralized with 39 ml of a 5% sodium hydroxide aqueous solution, and the acetonitrile was removed by distillation in vacuo therefrom. The residue was extracted three times with 50 ml of ethyl acetate, and the organic layer was washed with water. Then, the ethyl acetate was removed by distillation in vacuo therefrom. The resulting residue was purified by silica gel column chromatography (solvent; n-hexane:ethyl acetate 5:1) to obtain 3.60 g of a colorless liquid (yield 81%). Further, 0.77 g of 2-ethoxy-7-methoxychroman was recovered.

Reference Example 4

Recovery of Resorcinol

In Example 23, after the 2-ethoxy-7-hydroxychroman was extracted with chloroform, the resulting aqueous layer containing unreacted resorcinol was vacuum-concentrated to an amount of ½, and adjusted to a pH of 3 with the addition of 5 ml of 2 mol/liter hydrochloric acid aqueous solution. After extraction was conducted three times with 50 ml of ethyl acetate, the organic layer was washed with water, and the ethyl acetate was then removed by distillation in vacuo therefrom. The resulting residue was purified by distillation to obtain 2.71 g of resorcinol (recovery rate 27%).

Reference Example 5

Synthesis of N-[N-[3-(2-hydroxy-4-methoxyphenyl) propyl]-L-α-aspartyl]-L-phenylalanine 1-methyl ester A 500-milliliter egg plant type flask was charged with 3.60 g of 2-hydroxy-7-methoxychroman obtained in Example 26, 8.85 g of aspartame, 165 ml of methanol and 41 ml of water, and the inside of the system was purged with nitrogen (substitution of nitrogen). After 2.65 g of a 10% palladium carbon (water content 52%) was added thereto, the inside of the system was purged with hydrogen (substitution of hydrogen), and the mixture was stirred in a hydrogen atmosphere at 45° C. for 24 hours. After the reaction mixture was filtered, the filtrate was analyzed by high-performance liquid chromatography (HPLC), and showed that N-[N-[3-(2-hydroxy-4-methoxyphenyl) propyl]-L-α-aspartyl]-L-phenylalanine 1-methyl ester was formed in a yield of 68%.

Comparative Example 1

Synthesis of 2,7-dimethoxychroman

A 500-milliliter flask fitted with a dropping funnel was charged with 12.4 g of 3-methoxyphenol, 0.2 g of p-toluenesulfonic acid monohydrate and 100 ml of diethyl ether for dissolution, and the mixture was cooled with ice. To this solution was slowly added dropwise 14.3 g of acrolein dimethyl acetal under room temperature. After the dropwise addition, the solution was stirred for 3 hours while being cooled with ice. The reaction solution was alkalized with the addition of 5 ml of a 5% sodium hydroxide aqueous solution and 30 ml of water. Subsequently, 200 ml of diethyl ether was added thereto for extraction. Thus obtained organic layer was washed with 30 ml of water, the diethyl ether was removed by distillation in vacuo therefrom, and the resulting residue was purified by distillation to obtain 6.7 g of a colorless liquid (yield 32%).

Effects of the Invention:

According to the present process for producing an aspartame derivative, N-[N-[3-(2-hydroxy-substituted phenyl) propyl]-L-α-aspartyl]-L-phenylalanine 1-methyl ester derivative which is excellent as a sweetener and has a high degree of sweetness can be produced in a high yield with good efficiency by subjecting a 2-hydroxychroman derivative (3,4-dihydro-substituted-2H-1-benzopyran-2-ol derivative) having various substituents in a benzene ring and an aspartame to a reductive alkylation reaction.

According to the present process for purifying an aspartame derivative, an N-[N-[3-(2-hydroxy-4-substituted phenyl)propyl]-L-α-aspartyl]-L-phenylalanine 1-methyl ester derivative such as N-[N-[3-(2-hydroxy-4-methoxyphenyl)propyl]-L-α-aspartyl]-L-phenylalanine 1-methyl ester and the like which is especially excellent as a sweetener and has a high degree of sweetness can be obtained as a high-purity product. For example, crystals of high-purity of the desired compound can industrially be produced in a good yield and a good efficiency by crystallizing the desired compound through a crystallization step for purification from a solution, a solid or an intermediate therebetween such as a slurry, containing the derivative.

Further, this process can also be used as a process in which the derivative is purified and separated as a high purity form from a form of the derivative which includes impurity(ies), and is thus quite useful industrially.

Still further, according to the present invention, it is found that 2-alkoxy-7-methoxychroman(s) is quite useful as intermediates for the production of foods, pharmaceuticals and the like, especially as an intermediate for the production of N-[N-[3-(2-hydroxy-4-methoxyphenyl)propyl]-L-α-aspartyl]-L-phenylalanine 1-methyl ester excellent in stability and which may be used as a sweetener having a high degree of sweetness. Moreover, a process for industrially producing these intermediate(s) in high yield(s) at low cost(s) is provided, and novel dialkoxychroman derivatives especially useful as production intermediates are also be provided.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A process for producing a N-[N-[3-(2-hydroxy-substituted phenyl)propyl]-L-α-aspartyl]-L-phenylalanine 1-methyl ester compound represented by formula (2), said process comprising:

subjecting a 2-hydroxychroman compound represented by formula (1) and aspartame to a reductive alkylation reaction, to obtain said N-[N-[3-(2-hydroxy-substituted phenyl)propyl]-L-α-aspartyl]-L-phenylalanine 1-methyl ester compound:

wherein in formulas (1) and (2), $R_1$, $R_2$, $R_3$, and $R_4$, independently from each other, each represent a substituent selected from the group consisting of a hydrogen atom, a hydroxyl group, an alkoxy group having 1 to 3 carbon atoms, a benzyloxy group, an alkyl group having 1 to 3 carbon atoms, and a hydroxyalkyloxy group having 2 or 3 carbon atoms, and wherein $R_1$ and $R_2$ together, $R_3$ and $R_4$ together, or $R_2$ and $R_3$ together may represent a methylenedioxy group, with the proviso that in formula (2), none of $R_1$, $R_2$, $R_3$ and $R_4$ represents a benzyloxy group.

2. The process according to claim 1, wherein in said formulas (1) and (2), $R_2$ is a methoxy group, and $R_1$, $R_3$, and $R_4$ are hydrogen atoms.

3. The process according to claim 1, wherein in said formulas (1) and (2), $R_2$ is a hydroxyl group, and $R_1$, $R_3$, and $R_4$ are hydrogen atoms, with the proviso that in formula (1), $R_2$ may be a benzyloxy group.

4. The process according to claim 1, wherein in the said formulas (1) and (2), $R_2$ is a methyl group, and $R_1$, $R_3$, and $R_4$ are hydrogen atoms.

5. The process according to claim 1, wherein said reductive alkylation reaction is conducted in a solvent, and said solvent is at least one selected from the group consisting of methanol, ethanol, isopropyl alcohol, tetrahydrofuran, acetonitrile, acetic acid, ethyl acetate, mixtures thereof, and mixtures thereof with water.

6. The process according to claim 1, wherein said reductive alkylation reaction is conducted in the presence of a hydrogenation catalyst, and said catalyst is at least one selected from the group consisting of palladium based catalysts, platinum based catalysts, and rhodium based catalysts.

7. The process according to claim 1, wherein in said formulas (1) and (2), $R_1$, $R_2$, $R_3$, and $R_4$, independently from each other, each represent a substituent selected from the group consisting of a hydrogen atom, a hydroxyl group, a methoxy group, a benzyloxy group, a methyl group and a hydroxyalkyloxy group having 2 or 3 carbon atoms, and wherein $R_1$ and $R_2$ together, $R_3$ and $R_4$ together, and $R_2$ and $R_3$ together may represent a methylenedioxy group, with the proviso that in formula (2), none of $R_1$, $R_2$, $R_3$, and $R_4$ represents a benzyloxy group.

8. In a method for preparing a product having sweetness, which comprises adding a sweetener to said product, the improvement being that said sweetener is prepared by a process according to claim 1.

9. The method of claim 8, wherein said product is selected from the group consisting of foods, drinks, and pharmaceuticals.

\* \* \* \* \*